United States Patent [19]
Dubief et al.

[11] Patent Number: 5,792,448
[45] Date of Patent: Aug. 11, 1998

[54] USE OF FLAVONOIDS FOR PRESERVING AND/OR ENHANCING THE MECHANICAL PROPERTIES OF THE HAIR AND PROCESS FOR PROTECTING THE HAIR USING THESE COMPOUNDS

[75] Inventors: Claude Dubief, Le Chesnay; Damarys Braida-Valerio, Paris, both of France

[73] Assignee: L'Oreal, Paris, France

[21] Appl. No.: 866,041

[22] Filed: May 30, 1997

Related U.S. Application Data

[63] Continuation of Ser. No. 435,133, May 5, 1995, abandoned.

[30] Foreign Application Priority Data

May 5, 1994 [FR] France ................................ 94 05539

[51] Int. Cl.$^6$ ............................................. A61K 7/06
[52] U.S. Cl. ................................... 424/701; 514/456
[58] Field of Search ........................... 424/701; 514/456

[56] References Cited

U.S. PATENT DOCUMENTS

| | | | |
|---|---|---|---|
| 4,517,175 | 5/1985 | Iwabuchi et al. | 424/70 |
| 4,603,046 | 7/1986 | Georgalas et al. | 424/59 |

FOREIGN PATENT DOCUMENTS

| | | |
|---|---|---|
| A-0-275-005 | 7/1988 | European Pat. Off. |
| A-0545147 | 6/1993 | European Pat. Off. |
| A-2527927 | 12/1983 | France |
| A-2578422 | 9/1986 | France |
| 2687572 | 8/1993 | France |
| A-2687572 | 8/1993 | France |
| A-9414414 | 7/1994 | WIPO |

OTHER PUBLICATIONS

Zviak, Charles, Editor, The Science of Hair Care, "Hair Structure and Function", pp. 32–48 (1986).
Abstract of JP 5–4906 entitled "Cosmetic", in the name of T. Yarimizu.
Fichier Chemical Abstracts, vol. 121, n 163714, "Skin Cosmetics or Hair Preparations Containing Premna Integrifolia Extracts for UV Protection".
Derwent Abstract of FR-A-2687572.
Derwent Abstract of FR-A-2578422.
Derwent Abstract of EP-A-0545147.
Derwent Abstract of WO-A-9414414.
Derwent Abstract of JP-A-5017321.
Derwent Abstract of KR-B-9308763.

*Primary Examiner*—Jyothsan Venkat
*Attorney, Agent, or Firm*—Finnegan, Henderson, Farabow, Garrett & Dunner, L.L.P.

[57] ABSTRACT

The use of flavonoids for preserving and/or enhancing the mechanical properties of hair, and a process for protecting the mechanical properties of hair are disclosed.

21 Claims, 1 Drawing Sheet

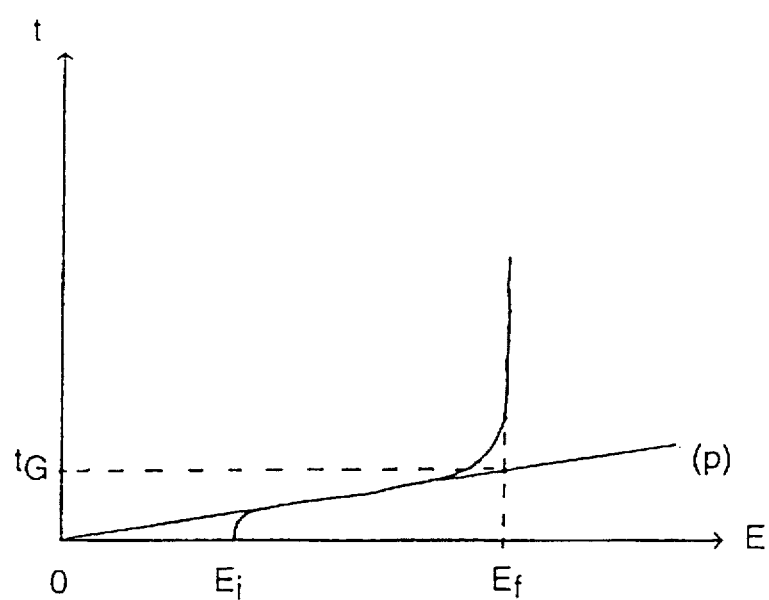

5,792,448

USE OF FLAVONOIDS FOR PRESERVING AND/OR ENHANCING THE MECHANICAL PROPERTIES OF THE HAIR AND PROCESS FOR PROTECTING THE HAIR USING THESE COMPOUNDS

This is a continuation of application Ser. No. 08/435,133, filed May 5, 1995, now abandoned.

The subject of the present invention is the use, in a cosmetic composition, of flavonoids as agents for protecting the mechanical properties of hair/keratin fibres from damage by environmental agents, and in particular from damage by light, and a process for protecting the hair from such damage.

It is well known that the hair is made sensitive or fragile to various degrees by the action of environmental agents and especially light, as well as by the repeated action of various hair treatments such as permanent waving, hair straightening, dyeing and bleaching. Numerous publications disclose that natural light destroys certain amino acids in the hair. Given that this damage impairs the hair fibre, it reduces the hair fibre's mechanical properties such as the tensile strength, the breaking load and the elasticity, or its resistance to swelling in an aqueous medium.

The tensile strength can be measured by the 15% extension plateau. The 15% extension plateau is the force which should be applied to wet hair of a given length in order to extend it permanently by 15%. The greater this force, the more elastic and resistant is the hair.

In order to combat the mechanical degradation of hair keratin by light, it has already been proposed to use certain substances capable of screening out light radiation, such as 2-hydroxy-4-methoxybenzophenone-5-sulphonic acid or its salts (FR-A-2,627,085) or 4-(2-oxo-3-bornylidenemethyl) benzenesulphonic acid or its salts (EP-A-329 032) or alternatively lactoferrin (FR-A-2,673,839), the disclosure of each of these documents is incorporated herein by reference.

However, it has now been discovered, unexpectedly and surprisingly, that flavonoids can also preserve and/or enhance the mechanical properties of the hair, and especially the tensile strength and the elasticity of the hair, in relation to different types of damage caused by environmental agents, and in particular light, to which the hair may be subjected.

It should be noted that certain flavonoids are known for their use in the preparation of cosmetic compositions, as agents for protecting the skin and/or its superficial growths from singlet oxygen, as described in French Patent Application FR-A-2,687,752, the disclosure of which is incorporated herein by reference. However, this document remains silent on the specific technical effects which could be obtained by application of flavonoids to the hair, in particular when the hair is subjected to damage by environmental agents or by light, or when subjected to the repeated action of hair treatments.

The subject of the present invention is therefore the use, in a cosmetic composition, of flavonoids as agents for protecting and/or enhancing the mechanical properties of the hair, and particularly the tensile strength of the hair, against damage by environmental agents, in particular against damage by light, and against damage due to the repeated action of hair treatments, to which the hair may be subjected.

More particularly, the present invention is directed to a method for the preservation and/or enhancement of at least one mechanical property of the hair, which comprises applying a cosmetically effective amount of a cosmetic composition comprising flavonoids to the hair for the purpose of protecting at least one mechanical property of the hair.

Flavonoids are compounds which occur in plant tissues. These compounds constitute different chemical categories, among which there may be mentioned flavanones, flavones, flavonols, dihydroflavonols, catechins, leucoanthocyanidins, chalcones, aurones and dihydrochalcones.

These flavonoids are known and particularly described in "The Flavonoids," Harborne J. B., Mabry T. J., Helga Mabry, 1975, pages 1 to 45, the disclosure of which is incorporated herein by reference.

According to the invention, flavonoids chosen from flavanones, flavones, flavonols, dihydroflavonols, catechins and leucoanthocyanidins are preferably used.

According to the invention, flavonoids corresponding to formula (I):

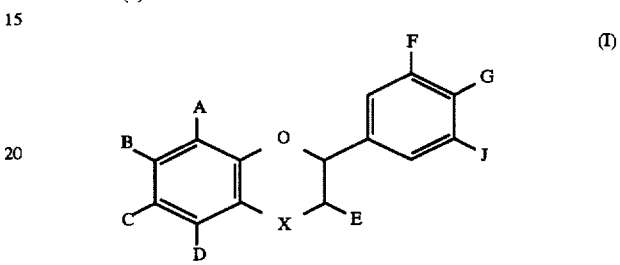

or (II):

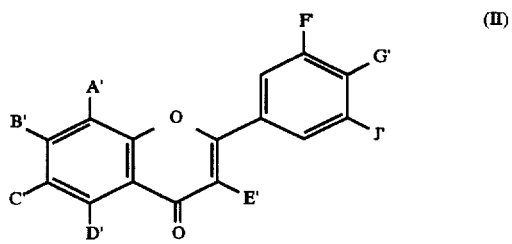

in which:

A,B,C and D, independently of each other, represent H or OH;

E represents H, OH or OR, wherein R represents:

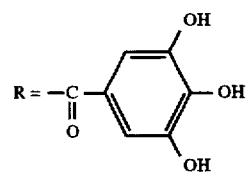

F, G, and J, independently of each other, represent H or OH; and X represents:

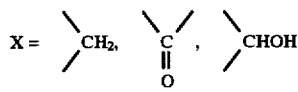

A', C' and D', independently of each other, represent H, OH or OCH$_3$;

E' represents H, OH or OR', where R' represents a radical of a sugar; and

B', F', G' and J', independently of each other, represent H, OH, OCH$_3$ or OCH$_2$-CH$_2$-OH, are preferably used.

Preferably, R' represents the 6—O—(6-deoxy-α-L-mannopyranosyl)-β-D-glucopyranosyl radical.

The compounds of formula (I) and (II) can be obtained according to the processes described in "The Flavonoids"

Harborne J. B., Mabry T. J., Helga Mabry, 1975, pages 1 to 45, the disclosure of which is incorporated herein by reference.

Within the framework of the present invention, the flavonoids more particularly preferred are chosen for example from taxifolin, catechin, epicatechin, eriodictyol, naringenin, rutin, troxerutin, chrysin, tangeretin, luteolin, epigallocatechin and epigallocatechin gallate.

In the compositions for use according to a method of the invention, the compounds of formula (I) and (II) are preferably present at a concentration which ranges from 0.001 to 10% by weight, and more preferably ranges from 0.005 to 5% by weight relative to the total weight of the composition.

The compounds may preferably be provided in the form of a single-phase or multi-phase aqueous or aqueous-alcoholic lotion, a single-phase or multi-phase gel, an emulsion, a cream, a vesicular dispersion, a foam or a spray.

The hair compositions in accordance with the invention may be provided in the form of a shampoo, a rinse-off or leave-in conditioner, a hair-styling foam, compositions for permanent waving, hair straightening, dyeing or bleaching, or alternatively in the form of rinse-off compositions to be applied before or after a dyeing, a permanent waving or a hair straightening or alternatively between the two stages of a permanent waving or a hair straightening.

The compositions moreover preferably contain conventional cosmetic additives chosen from fatty substances, organic solvents, silicones, thickeners, emollients, surfactants, anionic, cationic, non-ionic or amphoteric polymers, antifoaming agents, hair conditioning agents such as proteins, vitamins, treatment agents (agents for stopping hair loss, antidandruff agents), ceramids such as those mentioned in EP-A-500 437, the disclosure of which is incorporated herein by reference, colorants, pearling agents, sunscreening agents and especially sulphonic screening agents, perfumes, preservatives, antimicrobial agents, electrolytes, stabilizing agents such as erythorbic acid and sodium metabisulphite, sequestering agents and propelling agents.

More specifically, as fatty substances which may be contained in the compositions of the invention, there may be mentioned an oil, a wax, a mixture thereof, fatty acids, fatty alcohols, fatty acid esters such as triglycerides of $C_6$ to $C_{18}$ fatty acids, petroleum jelly, paraffin, lanolin, hydrogenated or acetylated lanolin.

Among the oils that may be used in accordance with the invention, there may preferably be mentioned mineral oils, animal oils, vegetable oils or synthetic oils, and especially liquid paraffin, paraffin oil, castor oil, jojoba oil, sesame oil, as well as silicon oils and gums, isoparaffins and fluorinated or perfluorinated oils.

Among the waxes that may be used in accordance with the invention, there may preferably be mentioned animal waxes, vegetable waxes, mineral waxes or synthetic waxes, and especially beeswax, candelilla wax, ozokerites, microcrystalline waxes as well as silicon waxes and resins.

Among the organic solvents normally used in the cosmetic compositions of the invention, there may preferably be mentioned more specifically lower $C_1$ to $C_6$ monoalcohols or polyalcohols such as ethanol, isopropanol, ethylene glycol, diethylene glycol, polyethylene glycol, and glycerol.

The thickening agents which may be used are preferably chosen from sodium alginate, gum arabic, cellulosic derivatives such as methylcellulose, hydroxymethylcellulose, hydroxyethyl cellulose, hydroxypropyl cellulose, hydroxypropyl methylcellulose, guar gum or its derivatives, xanthan gum, scleroglucans, and cross-linked polyacrylic acids.

As surfactants and as polymers, all those which are well known in the art, especially for their use in hair compositions, can be used.

Preferably, the compositions for use according to the invention do not contain any ginkgo extract.

The compositions of the invention may be provided in the form of a vesicular dispersion of ionic or non-ionic amphiphilic lipids. They are, in this case, prepared particularly by swelling the lipids in an aqueous solution so as to form spherules dispersed in the aqueous medium as described in STANDISH & WATKINS, *J. Mol. Biol.*, 13–238 (1965) or in French Patents FR-A-2,315,991 and FR-A-2,416,008 by the Applicant, the disclosure of each of which is incorporated herein by reference. The different types of preparation processes are described in "Les liposomes en biologie cellulaire et pharmacologie" (Liposomes in cell biology and pharmacology), Edition INSERM/John Libery Eurotext, 1987, pages 6 to 18, the disclosure of which is incorporated herein by reference.

The pH of the compositions according to the invention preferably ranges from 3 to 9, and more preferably ranges from 3 to 6.

The flavonoids may be added to the composition just before use. They are therefore, in this case, packaged separately from the other ingredients of the composition.

Another subject of the invention is a method for protecting the mechanical properties of the hair from damage by environmental agents, and in particular from light, which comprises applying to the hair an effective quantity of flavonoids as defined above, in a cosmetically acceptable carrier; this application being optionally followed by rinsing with water.

Several examples according to the invention will now be given by way of illustration and with no limitation being implied.

EXAMPLE 1

A leave-in treatment lotion of the following composition was prepared:

| | | |
|---|---|---|
| epicatechin | | 1.04 g |
| acetone | | 20.83 g |
| water | qs | 100 g |

This lotion was applied to highly bleached hair, and the swelling rate in water was then measured for the hair thus treated.

The swelling rate represents the rate of penetration of water into the hair. The variation of this rate, measured before and after a hair treatment, makes it possible to characterize the effects of the applied treatment: an increase in the swelling rate characterizes degradation of the hair, whereas a reduction in the swelling rate confirms the penetration into the hair of molecules of sufficiently small size provided by the applied treatment.

The initial thickness $E_i$ of the hair was measured on hair treated with the lotion according to the invention, with the aid of a sensor linked to a recorder. 0.1 ml of water was then placed on the hair with the aid of a syringe; swelling of the hair occurred. The sensor measured the thickness of the hair during the entire swelling phase. At the end of the phenomenon, the final thickness $E_f$ was measured.

FIG. 1 shows the curve of the recording obtained after a measuring operation: it gives the variation of the thickness (E) of the hair as a function of time (t)

In order to determine the swelling time $t_G$, the slope at the origin (p) of the curve was plotted. The intersection of this slope with the line at the final thickness determines the moment of the end of the swelling phenomenon.

The swelling rate is then determined by the equation:

swelling rate=$(E_f-E_i)/t_G$

The swelling rate of hair treated with the lotion according to the invention was compared to that of untreated hair. It was observed that the swelling rate of the hair treated according to the invention had decreased by 49.9% compared with that of the untreated hair.

EXAMPLE 2

A leave-in treatment lotion of the following composition was prepared:

| | | |
|---|---|---|
| taxifolin | | 1.04 g |
| acetone | | 20.83 g |
| water | qs | 100 g |

This lotion was applied to highly bleached hair and the swelling rate was measured in water as described in Example 1. It was observed that the swelling rate of the hair treated according to the invention had decreased by 73.4% compared with that of the untreated hair.

What is claimed is:

1. A method for the preservation and/or enhancement of at least one mechanical property of the hair, wherein said at least one mechanical property is tensile strength, breaking load, elasticity or resistance to swelling in an aqueous medium, said method comprising applying a cosmetically effective amount of a cosmetic composition comprising at least one flavonoid to said hair for the purpose of protecting said at least one mechanical property.

2. The method according to claim 1, wherein said at least one mechanical property of the hair is tensile strength or elasticity.

3. The method according to claim 1, wherein said at least one mechanical property of the hair is preserved or enhanced in relation to the different types of damage caused by environmental agents to which said hair is subjected.

4. The method according to claim 1, wherein said at least one mechanical property of the hair is preserved or enhanced in relation to the repeated action of hair treatment.

5. The method according to claim 1, wherein said at least one mechanical property of the hair is preserved or enhanced in relation to damage by light.

6. The method according to claim 1, wherein said flavonoids are flavanones, flavones, flavonols, dihydroflavonols, catechins or leucoanthocyanidins.

7. A method for the preservation and/or enhancement of at least one mechanical property of the hair, wherein said at least one mechanical property is tensile strength, breaking load, elasticity or resistance to swelling in an aqueous medium, said method comprising applying a cosmetically effective amount of a cosmetic composition comprising at least one flavonoid to said hair for the purpose of protecting at least one mechanical property of said hair, wherein said at least one flavonoid is taxifolin, catechin, epicatechin, eriodictyol, naringenin, epigallocatechin, or epigallocatechin gallate.

8. A method for the preservation and/or enhancement of at least one mechanical property of the hair, wherein said at least one mechanical property is tensile strength, breaking load, elasticity or resistance to swelling in an aqueous medium, said method comprising applying a cosmetically effective amount of a cosmetic composition comprising at least one flavonoid to said hair for the purpose of protecting at least one mechanical property of said hair, wherein said at least one flavonoid is rutin, troxerutin, chrysin, tangeretin or luteolin.

9. A method for the preservation and/or enhancement of at least one mechanical property of the hair, wherein said at least one mechanical property is tensile strength, breaking load, elasticity or resistance to swelling in an aqueous medium, said method comprising applying a cosmetically effective amount of a cosmetic composition comprising at least one flavonoid to said hair for the purpose of protecting at least one mechanical property of said hair, wherein said at least one flavonoid is a compound of formula (I):

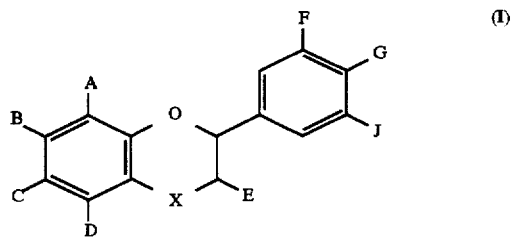

or (II):

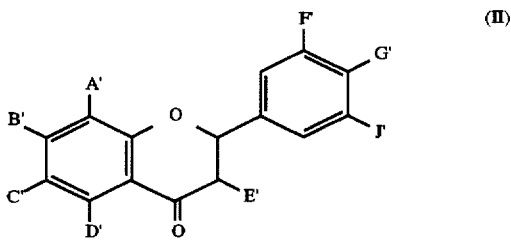

in which:

A, B, C, and D, independently of each other, represent H or OH;

E represents H, OH, or OR, wherein R represents:

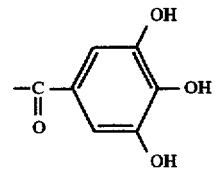

F, G, and J, independently of each other, represent H or OH; and X represents:

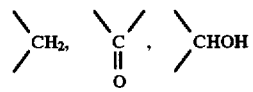

A', C', and D', independently of each other, represent H, OH, or $OCH_3$;

E' represents H, OH, or OR', wherein R' represents a radical of 6—O—(6-deoxy-α-L-mannopyranosyl)-β-D-glucopyranosyl; and B', F', G' and J', independently of each other, represent H, OH, $OCH_3$ or $OCH_2$—$CH_2$—OH.

10. The method according to claim 1, wherein said at least one flavonoid is present, in a cosmetically acceptable carrier, at a concentration which ranges from 0.001% to 10% by weight.

11. The method according to claim 10, wherein said at least one flavonoid is present, in a cosmetically acceptable carrier, at a concentration which ranges from 0.005% to 5% by weight.

12. The method according to claim 1, wherein said cosmetic composition comprising said at least one flavonoid is provided in the form of an aqueous or aqueous-alcoholic lotion, a gel, a cream, an emulsion, a vesicular dispersion, a foam or a spray.

13. The method according to claim 1, wherein said cosmetic composition comprising said at least one flavonoid is provided in the form of a shampoo; a rinse-off or leave-in conditioner; a composition for permanent waving, hair straightening, dyeing or bleaching; a rinse-off composition to be applied before or after a dyeing, a permanent waving or a hair straightening; or a rinse-off composition to be applied between the two stages of a permanent waving or a hair straightening.

14. The method according to claim 1, wherein said cosmetic composition comprising said at least one flavonoid additionally contains at least one cosmetically acceptable additive.

15. The method according to claim 1, wherein said cosmetic composition does not contain any ginkgo extract.

16. The method according to claim 1, wherein said at least one flavonoid is packaged separately from any other component of said composition and is added to said composition just prior to use.

17. A method for protecting at least one mechanical property of the hair against damage caused by environmental agents, which comprises applying an effective amount of at least one flavonoid, in a cosmetically acceptable carrier, to said hair for the purpose of protecting at least one mechanical property thereof, wherein said at least one mechanical property is tensile strength, breaking load, elasticity or resistance to swelling in an aqueous medium.

18. The method according to claim 1, wherein said hair is damaged.

19. The method according to claim 18, wherein said damage is caused by action of at least one environmental agent or action of repeated hair treatments.

20. The method according to claim 19, wherein said at least one environmental agent is natural light.

21. The method according to claim 19, wherein said hair treatments are permanent waving, hair straightening, dyeing or bleaching.

\* \* \* \* \*